United States Patent [19]

Brambilla et al.

[11] Patent Number: 4,839,363

[45] Date of Patent: Jun. 13, 1989

[54] ERGOLINYL HETEROCYCLES FOR THE TREATMENT OF PARKINSON'S DISEASE AND DYSKINETIC SYMPTOMS

[75] Inventors: Enzo Brambilla, Mariano Comense; Sergio Mantegani; Lorenzo Pegrassi, both of Milan; Alessandro Rossi; Aldemio Temperilli, both of Milan, all of Italy

[73] Assignee: Farmitalia Carlo Erba, Milan, Italy

[21] Appl. No.: 149,012

[22] Filed: Jan. 27, 1988

[30] Foreign Application Priority Data

Feb. 3, 1987 [GB] United Kingdom ............... 8702364

[51] Int. Cl.[4] ................... A61K 31/48; C07D 457/02
[52] U.S. Cl. .................... 514/288; 514/256; 514/275; 544/331; 544/333; 546/67
[58] Field of Search ............ 546/67; 514/288, 275, 514/256; 544/331, 333

[56] References Cited

U.S. PATENT DOCUMENTS

| | | | |
|---|---|---|---|
| 2,725,384 | 11/1955 | Burness | 548/373 |
| 4,632,928 | 12/1986 | Retlegi et al. | 546/67 |
| 4,657,914 | 4/1987 | Bernardi et al. | 546/67 |
| 4,690,929 | 9/1987 | Bernardi et al. | 546/67 |
| 4,713,457 | 12/1987 | Ohno et al. | 546/67 |

FOREIGN PATENT DOCUMENTS

| | | | |
|---|---|---|---|
| 128479 | 12/1984 | European Pat. Off. | 546/67 |
| 154897 | 4/1982 | Fed. Rep. of Germany | |
| 238794 | 9/1986 | Fed. Rep. of Germany | 546/67 |
| 1238794 | 9/1986 | Fed. Rep. of Germany | |
| 2120242 | 11/1983 | United Kingdom | 546/67 |

OTHER PUBLICATIONS

Bernardi et al., CA 74–42536n, 1971, "Methyl O-methyl–lumilysergati".
Krepelka et al., CA 98–179705g, 1983, "Ergotic alkaloids, LXVII, 8-substitution derivatives of D-6-methylergoline-I".
Roensch et al., CA107–40180t, 1987, "Preparation of oxazolidinylergolines".
Roensch et al., Ca 108–22135y, 1988, "Preparation of oxazolinylergolines as antihypertensive".
Rucman, Heterocycles, vol. 20, No. 11, 1983, pp. 2229–2232, "Thermal Decomposition of Dihydroergocristine Methanesulphonate".
Neef et al., J. Org. Chem., 1981, 46, pp. 2824–2826, "One step conversions of esters of 2-imidazolines, benzimidazolines, and benzothiazoles by aluminum organic reagents".
Crider et al., J. Med. Chem, 1977, vol. 20, No. 11, pp. 1473–1477, "Ergot Alkaloids, Synthesis of 6-alkyl-8--ergolines and 6-methyl-8-aminoergolines as potent prolactin inhibitors".

Krepelka et al., Collect. Czech. Chem. Commun., 48, 312–318 (1983).

Primary Examiner—Donald G. Daus
Assistant Examiner—Cecilia Shen
Attorney, Agent, or Firm—Oblon, Spivak, McClelland, Maier & Neustadt

[57] ABSTRACT

Ergoline derivatives of the formula I

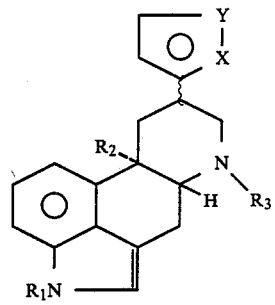

wherein $R_1$ represents a hydrogen atom or a methyl group;
$R_2$ represents a hydrogen atom or a methoxy group;
$R_3$ represents a hydrocarbon group having from 1 to 4 carbon atoms;
X represents a nitrogen atom and Y represents an oxygen atom, a

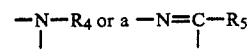

group wherein $R_4$ represents a hydrogen atom, a $C_1$–$C_4$ alkyl or a phenyl group, $R_5$ represents a hydrogen atom, a $C_1$–$C_4$ alkyl, a phenyl, an amino or di($C_1$–$C_4$ alkyl)amino group and the nitrogen atom of the group

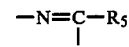

is not joined to the nitrogen atom represented by X, or Y represents a nitrogen atom and X represents an oxygen atom or a

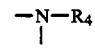

group wherein $R_4$ is as above defined; and the pharmaceutically acceptable salt thereof; are useful for treatment of Parkinsonism and dyskinetic symptoms.

10 Claims, No Drawings

ERGOLINYL HETEROCYCLES FOR THE TREATMENT OF PARKINSON'S DISEASE AND DYSKINETIC SYMPTOMS

BACKGROUND OF THE INVENTION

1. Field of the Invention

The present invention relates to ergoline derivatives which are effective in the central nervous system (CNS) and are useful as anti-Parkinson agents.

2. Brief Description of the Background:

The inventors are not aware of any prior disclosures of the ergoline derivatives disclosed herein.

SUMMARY OF THE INVENTION

The present invention provides compounds of formula I

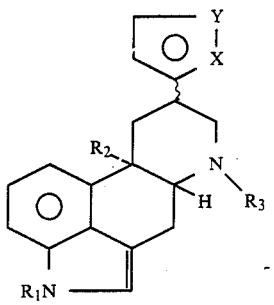

wherein $R_1$ represents a hydrogen atom or a methyl group;
$R_2$ represents a hydrogen atom or a methoxy group;
$R_3$ represents a hydrocarbon group having from 1 to 4 carbon atoms; and
X represents a nitrogen atom and Y represents an oxygen atom, a

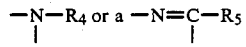

group wherein $R_4$ represents a hydrogen atom, a $C_1$–$C_4$ alkyl or a phenyl group, $R_5$ represents a hydrogen atom, a $C_1$–$C_4$ alkyl, a phenyl, an amino or a di($C_1$–$C_4$ alkyl) amino group and the nitrogen atom of the group

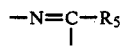

is not joined to the nitrogen atom represented by X, or Y represents a nitrogen atom and X represents an oxygen atom or a

group wherein $R_4$ is as above defined; and pharmaceutically acceptable salts of such ergoline derivatives.

The ergoline derivatives of the formula I and their pharmaceutically acceptable salts are useful in therapy, particularly in the therapy of extrapyramidal syndromes such as Parkinson's disease and dyskinetic symptoms.

Furthermore, in three other aspects, the invention concerns methods for treating extrapyramidal syndromes such as Parkinson's disease and dyskinetic symptoms in a subject, pharmaceutical compositions and methods for preparing medicaments useful for these purposes, which methods and compositions employ compounds of formula I or their pharmaceutically acceptable salts.

DESCRIPTION OF THE PREFERRED EMBODIMENTS

In the definition of $R_3$, a "hydrocarbon group having from 1 to 4 carbon atoms" is intended to include alkyl, cycloalkyl and unsaturated (both ethylenically and acetylenically) groups. Representative groups include methyl, ethyl, n-propyl, isopropyl, butyl, t-butyl, isobutyl, methylcyclopropyl, allyl and propargyl.

In the definitions of $R_4$ and $R_5$, a "$C_1$–$C_4$ alkyl group" is intended to include methyl, ethyl, n-propyl, i-propyl, butyl, t-butyl and i-butyl groups. Preferably, $R_4$ denotes methyl. Preferably, $R_5$ denotes methyl. When $R_5$ is a di($C_1$–$C_4$ alkyl)amino group, preferably it is dimethylamino.

"Pharmaceutically acceptable salts" refers to those salts which retain the biological effectiveness and properties of the free bases and which are not biologically or otherwise undesirable, formed with inorganic acids such as hydrochloric, hydrobromic, sulfuric, nitric or phosphoric acid; and organic acids such as acetic, propionic, glycolic, pyruvic, oxalic, malic, malonic, succinic, maleic, fumaric, tartaric, citric, benzoic, cinnamic, mandelic, methanesulfonic, ethanesulfonic, p-toluenesulfonic or salicylic acid.

Preferred compounds of the invention are those in which $R_1$ and $R_2$ are hydrogen atoms, $R_3$ is a methyl group, X is a nitrogen atom and Y is an oxygen atom, a

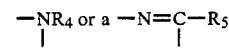

group wherein $R_4$ represents hydrogen atom, a $C_1$–$C_4$ alkyl or phenyl group and $R_5$ represents a $C_1$–$C_4$ alkyl or amino group, or Y represents a nitrogen atom and X is an oxygen atom or a

group wherein $R_4$ is as defined immediately above.

The invention further provides a process for preparing the compounds of the formula I as defined above, which process is characterized by reacting a compound of the formula II

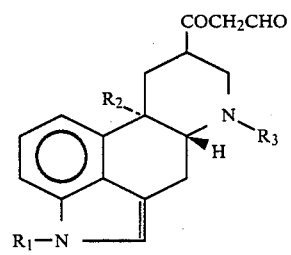

wherein $R_1$, $R_2$ and $R_3$ are as above defined, with a compound of the formula A-NH$_2$ wherein A represents a group of the formula

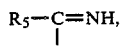

a hydroxy group or a group of the formula —NHR$_4$, wherein $R_4$ and $R_5$ are as above defined.

The reaction is preferably carried out in a protic solvent such as an alcohol or an organic acid, most preferably in ethanol or acetic acid, at a temperature of from 0° to 100° C. for a period of from 5 minutes to 60 hours. The crude product may be purified by crystallization, salt formation, or by chromatography on a silica gel column. The ergoline derivative of formula (I) may therefore be converted into a pharmaceutically acceptable salt if desired.

The ergoline-8-propionaldehyde II may be prepared by established procedures starting from the corresponding 8β-acetyl ergolines (Bernardi et al, Gazz. Chim. It., p. 961, 94, 1964).

The ergoline derivatives according to the invention and their pharmaceutically acceptable salts are useful in the therapy of extrapyramidal syndromes such as Parkinson's disease and dyskinetic symptoms. By "dyskinetic symptoms" is meant disordered movements of voluntary or involuntary muscles, due to disorders of the extrapyramidal system (i.e. extrapyramidal syndromes), such as Parkinsonism, tardive diskinesia induced by long-term administration of neuroleptic agents, Huntington's chorea, etc. Thus, the inventive compounds may also be used for the making of medicaments effective against extrapyramidal syndromes. Accordingly, the invention also provides a pharmaceutical composition comprising an ergoline derivative having the general formula I or a pharmaceutically acceptable salt thereof in admixture with a pharmaceutically acceptable diluent or carrier. The present invention also relates to methods of treating Morbus Parkinson and dyskinetic symptoms using said compounds, said compositions or medicaments.

BIOLOGICAL TESTS AND DOSES

The profile of dopamine agonists of the compound of the formula I was preliminarily assessed in vitro by binding assays to receptors of rat cerebral tissue (e.g. SCHWARCZ, R. et al, Nature, 271: 766, 1978), where they showed affinity for the dopamine D-2 receptors, at a concentration of about $10^{-8}$M.

In vivo interaction studies with the specific D-1 antagonist SCH 23390 and with the specific D-2 antagonist 1-sulpiride in the Ungerstedt's rotational model in the rat (Ungerstedt, U., Acta Physiol. Scand., Suppl. 367: 69, 1971) unexpectedly proved that the title compounds are highly specific functional D-1 agonists at a dosage of from 0.5 to 1 mg/kg s.c. The orientative acute toxicity of the compounds I in rats is higher than 400 mg/kg p.o.

The compounds are therefore indicated for use as anti-parkinson agents and as therapeutic agents in dyskinetic symptoms. The amount of active compound for this indication will, of course, be dependent on the subject being treated, the severity of the application, the manner of administration and the judgment of the prescribing physician.

However, an effective dosage is in the range of about 0.2 to about 10 mg, conveniently given in divided doses 2 to 4 times a day in unit dosage form containing from about 0.10 to about 5 mg of the compound or in sustained release form.

ADMINISTRATION AND COMPOSITIONS

Administration of the active compound and salts described herein can be via any of the accepted modes of administration for anti-parkinson agents. These methods include oral and parenteral modes, preferably oral administration.

Depending on the intended mode, such compositions may be formulated in conventional manner so as to be, for example, a solution or a tablet.

The composition will include a conventional pharmaceutical carrier or excipient and an active compound of formula I or the pharmaceutically acceptable salts thereof and, in addition, may include other medicinal agents, pharmaceutical agents, carriers, adjuvants, etc.

For solid composition, conventional non-toxic solid carriers include, for example, pharmaceutical grades of mannitol, lactose, starch magnesium stearate, sodium saccharin, talcum, cellulose, glucose, sucrose, magnesium carbonate and the like may be used. Liquid pharmaceuticlly administerable compositions can, for example, be prepared by dissolving, dispersing, etc., an active compound as defined above and an optional pharmaceutical adjuvant in a carrier, such as, for example, water saline, aqueous dextrose, glycerol, ethanol and the like, to thereby form a solution or suspension.

The compound of Example 2 hereinafter is the preferred compound, and the preferred activity is anti-parkinson activity.

The invention now being generally described, the same will be better understood by reference to certain specific examples which are included herein for purposes of illustration only and are not intended to be limiting of the invention or any embodiment thereof, unless specified.

EXAMPLE 1 (FCE 21642)

6-Methyl-8β-(1-methyl-pyrazol-5-yl)-ergoline (I, $R_1=R_2=H$, $R_3=R_4=CH_3$, X=NR$_4$, Y=N)

(a) 3-oxo-3-(6-Methyl ergolin-8β-yl)-propionaldehyde.

To a suspension of 10.8 g (0.2 mole) of sodium methoxide in 150 ml of toluene was added a solution of 26.8 g (0.1 mole) of 8β-acetyl ergoline in 200 ml of toluene while stirring and cooling (icy water).

After 30 minutes, 10 ml of ethyl formate was added dropwise and stirring was continued for 5 hours.

The resulting suspension of sodium enolate was filtered off, washed with toluene and dissolved in icy water.

The basic aqueous solution was extracted with ethyl acetate to remove the unreacted 8β-acetyl ergoline, then acidified with acetic acid and extracted several times with ethyl acetate. The organic solution was dried over Na$_2$SO$_4$ and evaporated to dryness, affording 23 g of the title compound as clear yellow foam, yield 77%.

(b) 6-Methyl-8β-(1 methyl-pyrazol-5-yl)-ergoline.

A solution of 5 g (0.017 mole) of 3-oxo-3-6-methylergolin-8β-yl)-propionaldehyde and methylhydrazine in 100 ml of ethanol was refluxed for 2 hours. After cooling, the product was filtered off, washed with ethanol, and dried to give the title compound, 1.5 g, m.p. 218°-220° C.

EXAMPLE 2 (FCE 21641)

6-Methyl-8β-(1-methyl-pyrazol-3-yl)-ergoline (I, $R_1=R_2=H$, $R_3=R_4=CH_3$, $X=N$, $Y=NR_4$)

The mother liquors obtained in Example 1 after separation of 6-Methyl-8β-(1-methyl-3-pyrazolyl)-ergoline, were chromatographed on silica gel using ethyl acetate/cyclohexane 2/1 as eluent to give the title compound, 1.7 g, m.p. 243°–246° C.

EXAMPLE 3

6-Methyl-8β-(isoxazol-5-yl)-ergoline (I, $R_1=R_2=H$, $R_3=CH_3$, $X=O$, $Y=N$)

A mixture of 5 g (0.017 mole) of 3-oxo-3-(6-methylergolin-8β-yl)-propionaldehyde in 100 ml of glacial acetic acid and 5 g of hydroxylamine hydrochloride was stirred for 20 hours at room temperature and then poured in ice-cold water. After basification with ammonium hydroxide, the solid which separated was filtered and dissolved in ethyl acetate. The organic solution was washed with brine, dried and the solvent was removed, and the residue was crystallized twice from acetone affording the title compound, 1.8 g; m.p. 132°–134° C.

EXAMPLE 4

6-Methyl-8β-(isoxazol-3-yl)-ergoline ($R_1=R_2=H$, $R_3=CH_3$, $X=N$, $Y=O$)

The mother liquors obtained in Example 3 were chromatographed on silica gel using acetone/cyclohexane 1/5 as eluent giving the title compound, 0.3 g, m.p. 182°–185° C.

EXAMPLE 5 (FCE 21643)

6-Methyl-8β-(pyrazol-3-yl)-ergoline ($R_1=R_2=R_4=H$, $R_3=CH_3$, $X=NR_4$, $Y=N$)

Operating as in Example 1, but employing hydrazine instead of methyl hydrazine, the title compound was obtained in 75% yield, m.p. 160°–162° C.

EXAMPLE 6 (FCE 21639)

6-Methyl-8β-(1-phenyl-pyrazol-5-yl)-ergoline ($R_1=R_2=H$, $R_3=CH_3$, $X=NR_4$, $R_4=Ph$, $Y=N$)

Operating as in Example 1, but employing phenylhydrazine of methylhydrazine the title compound was obtained, m.p. 256°–158° C.

EXAMPLE 7 (FCE 21640)

6-Methyl-8β-(1-phenyl-pyrazol-3-yl)-ergoline ($R_1=R_2=H$, $R_3=CH_3$, $X=N$, $Y=NR_4$, $R_4=Ph$)

The mother liquors obtained in Example 6 were chromatographed on silica gel using ethyl acetate/cyclohexane 1/4 as eluent to give the title compound, m.p. 234°–236° C.

EXAMPLE 8

6-Methyl-8β-(2-amino-pyrimidin-4-yl)-ergoline ($R_1=R_2=H$, $R_3=CH_3$, $X=N$,

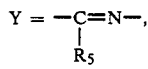

$R_5=NH_2$)

Operating as in Example 1, but employing guanidine instead of methyl hydrazine the title compound was obtained in 42% yield.

EXAMPLE 9

6-Methyl-8β-(2-methyl-pyridimidin-4-yl)-ergoline ($R_1=R_2=H$, $R_3=R_5=CH_3$, $X=N$,

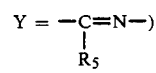

Operating as in Example 1, but employing acetamidine instead of methyl hydrazine the title compound was obtained in 60% yield.

The compounds of the invention can be prepared in typical formulations, and for example the following are representative, the active ingredient being one of the pharmacologically active compounds.

EXAMPLE 10

| Tablet | Active ingredient | 5 mg |
|---|---|---|
| | Dried starch | 300 mg |
| | Polivinylpyrrolidone | 50 mg |
| | Sodium carboxymethyl starch | 50 mg |
| | Stearic acid | 20 mg. |

The active ingredient and starch are mixed together and mixed with a solution of polivinylpyrrolidone in alcohol. The mixture is extruded through a screen, dried, sized and mixed with sodium carboxymethyl starch and stearic acid prior to compression on a tablet machine. Tablets weighing 425 mg are obtained.

EXAMPLE 11

| Capsules | Active ingredient | 0.10 mg |
|---|---|---|
| | Starch (flowable) | 50 mg |
| | Silicone fluid | 0.5 mg. |

A portion of the starch is mixed with the silicone fluid. To the power is added the active ingredient and the remainder of the starch. The blended mixture is filled into hard gelatin capsules.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A method of treatment of Parkinson's disease, which comprises administering to a patient in need of said treatment a therapeutically effective amount of an ergoline derivative having the formula I

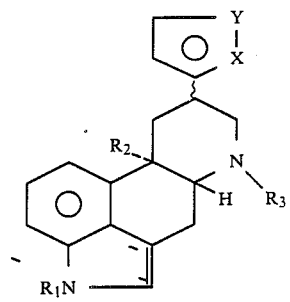

wherein $R_1$ represents a hydrogen atom or a methyl group;

$R_2$ represents a hydrogen atom or a methoxy group;

$R_3$ represents a hydrocarbon group which is one member selected from the group consisting of methyl, ethyl, n-propyl, isopropyl, butyl, t-butyl, isobutyl, methylcyclopropyl, allyl and propargyl;

X represents a nitrogen atom and Y represents an oxygen atom, a

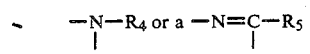

group wherein $R_4$ represents a hydrogen atom, a $C_1$–$C_4$ alkyl, or a phenyl group, $R_5$ represents a hydrogen atom, a $C_1$–$C_4$ alkyl, a phenyl, an amino or di($C_1$–$C_4$ alkyl)amino group and the nitrogen atom of the group

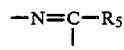

is not joined to the nitrogen atom represented by X, or Y represents a nitrogen atom and X represents an oxygen atom or a

group wherein $R_4$ is defined as above; and pharmaceutically acceptable salts thereof.

2. The method of claim 1, wherein $R_1$ and $R_2$ are hydrogen atoms, $R_3$ is methyl, X is a nitrogen atom and Y is an oxygen atom, a

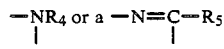

group wherein $R_4$ represents a hydrogen atom, a $C_1$–$C_4$ alkyl or a phenyl group and $R_5$ represents a $C_1$–$C_4$ alkyl or amino group, or Y represents a nitrogen atom and X is an oxygen atom or a

group, wherein $R_4$ is as defined herein.

3. The method of claim 2, wherein $R_4$ is methyl.

4. The method of claim 1, wherein $R_4$ is methyl.

5. The method of claim 1, wherein said ergoline derivative is 6-methyl-8β-(1-methylpyrazol-3-yl)-ergoline.

6. A method of treatment of dyskinetic symptoms, which comprises administering to a patient in need of said treatment a therapeutically effective amount of an ergoline derivative having the formula I

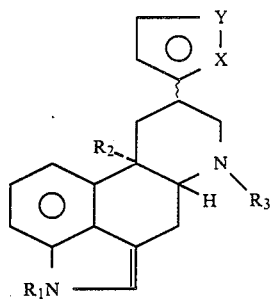

wherein $R_1$ represents a hydrogen atom or a methyl group;

$R_2$ represents a hydrogen atom or a methoxy group;

$R_3$ represents a hydrocarbon group which is one member selected from the group consisting of methyl, ethyl, n-propyl, isopropyl, butyl, t-butyl, isobutyl, methylcyclopropyl, allyl and propargyl;

X represents a nitrogen atom and Y represents an oxygen atom, a

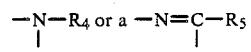

group wherein $R_4$ represents a hydrogen atom, a $C_1$–$C_4$ alkyl, or a phenyl group, $R_5$ represents a hydrogen atom, a $C_1$–$C_4$ alkyl, a phenyl, an amino or di($C_1$–$C_4$ alkyl)amino group and the nitrogen atom of the group

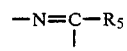

is not joined to the nitrogen atom represented by X, or Y represents a nitrogen atom and X represents an oxygen atom or a

group wherein $R_4$ is defined as above; and pharmaceutically acceptable salts thereof.

7. The method of claim 6, wherein $R_1$ and $R_2$ are hydrogen atoms, $R_3$ is methyl, X is a nitrogen atom and Y is an oxygen atom, a

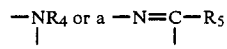

group wherein $R_4$ represents a hydrogen atom, a $C_1$–$C_4$ alkyl or a phenyl group and $R_5$ represents a $C_1$–$C_4$ alkyl or amino group, or Y represents a nitrogen atom and X is an oxygen atom or a

group, wherein $R_4$ is as defined herein.
8. The method of claim 7, wherein $R_4$ is methyl.
9. The method of claim 6, wherein $R_4$ is methyl.
10. The method of claim 6, wherein said ergoline derivative is 6-methyl-8β-(1-methylpyrazol-3-yl)-ergoline.